United States Patent [19]

Weidenburner

[11] Patent Number: 5,022,391
[45] Date of Patent: Jun. 11, 1991

[54] KNEE ORTHOSIS

[76] Inventor: William K. Weidenburner, 9903 Melgar Dr., Whittier, Calif. 90603

[21] Appl. No.: 361,320

[22] Filed: Jun. 5, 1989

[51] Int. Cl.$^5$ .............................................. A61F 5/00
[52] U.S. Cl. ................................. 128/80 F; 128/80 C
[58] Field of Search ...................... 128/77, 80 R, 80 F, 128/80 C, 89 R; 623/27, 39, 44

[56] References Cited

U.S. PATENT DOCUMENTS

| | | | |
|---|---|---|---|
| 3,680,549 | 8/1972 | Lehneis et al. | 128/89 R X |
| 3,902,482 | 9/1975 | Taylor | 623/39 X |
| 4,340,041 | 7/1982 | Frank | 128/80 C |
| 4,361,142 | 11/1982 | Lewis et al. | 128/80 C |
| 4,428,369 | 1/1984 | Peckham et al. | 128/80 C |
| 4,572,170 | 2/1986 | Cronk et al. | 128/80 C |
| 4,628,916 | 12/1986 | Lerman et al. | 623/39 X |
| 4,643,176 | 2/1987 | Mason et al. | 128/80 C |
| 4,715,363 | 12/1987 | Detty | 128/80 C |
| 4,723,539 | 2/1988 | Townsend | 128/80 C |
| 4,773,404 | 9/1988 | Townsend | 128/80 C |
| 4,821,707 | 4/1989 | Audette | 128/80 C X |
| 4,928,670 | 5/1990 | DeLorenzo | 128/89 R X |

Primary Examiner—Richard J. Apley
Assistant Examiner—Linda C. M. Dvorak
Attorney, Agent, or Firm—Edgar W. Averill, Jr.

[57] ABSTRACT

An improved knee orthosis of the type having a femoral shell, having a medial femoral upright and a lateral femoral upright affixed thereto. A tibial shell has a medial tibial upright and a lateral tibial upright affixed thereto, and these two pairs of uprights are hinged together. The improvement of the present invention relates to the hinge construction and to the spiral shape of the tibial shell which aids in the stabilization of the tibia. The hinge utilizes two pins at the base of the femoral upright and two pins near the top of the tibial upright. The anterior tibial pin and the anterior femoral pin are affixed to a first link plate in a pivotal manner. Similarly, the posterior femoral pin and the posterior tibial pin are linked to a second link plate on the opposite side of the hinge.

18 Claims, 3 Drawing Sheets

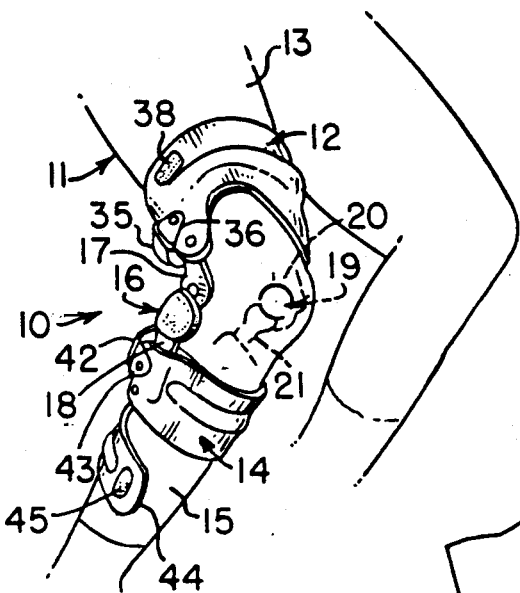
FIG. 1.
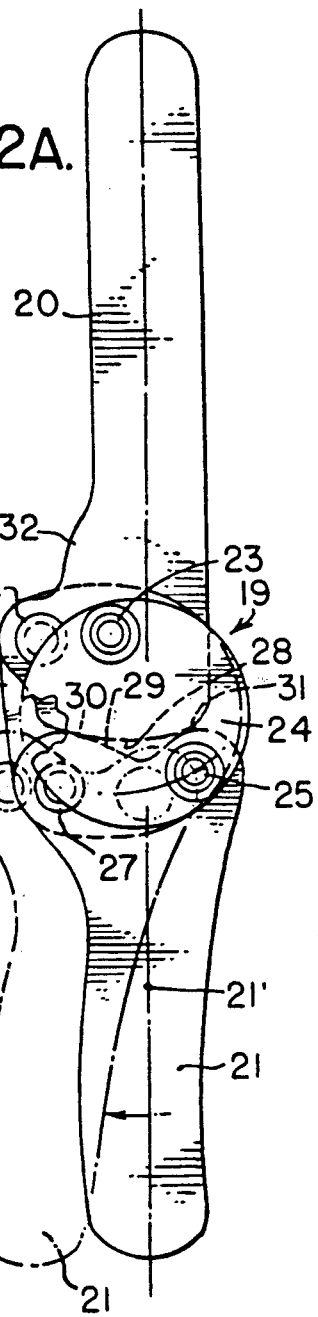
FIG. 2A.
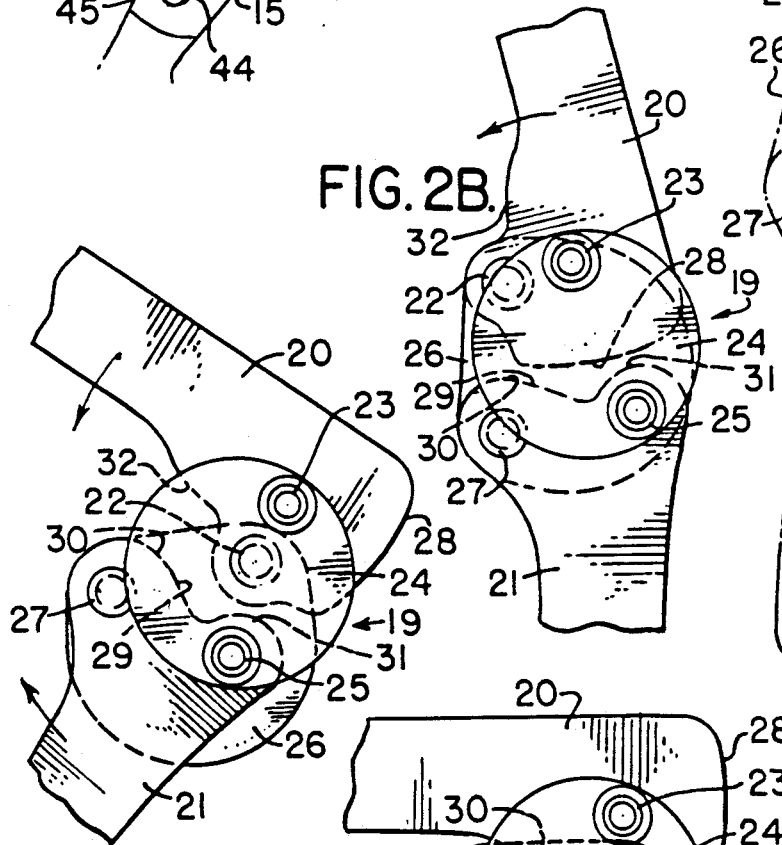
FIG. 2B.
FIG. 2C.
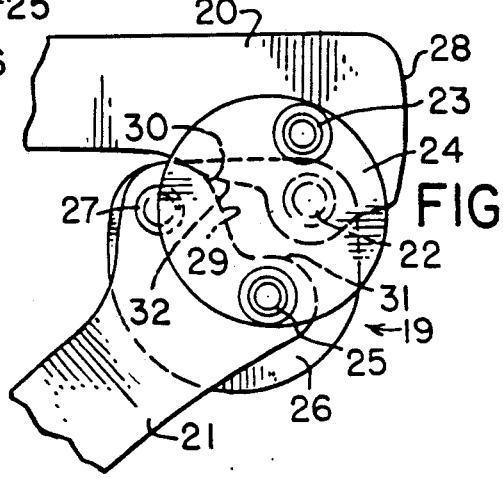
FIG. 2D.

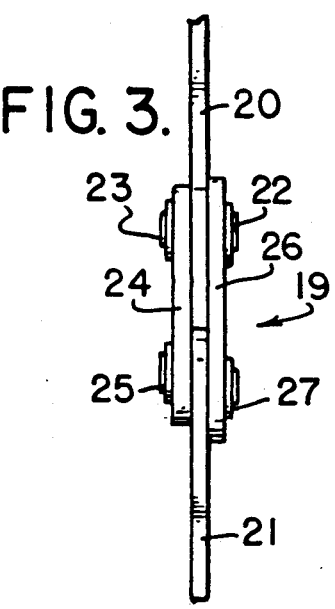
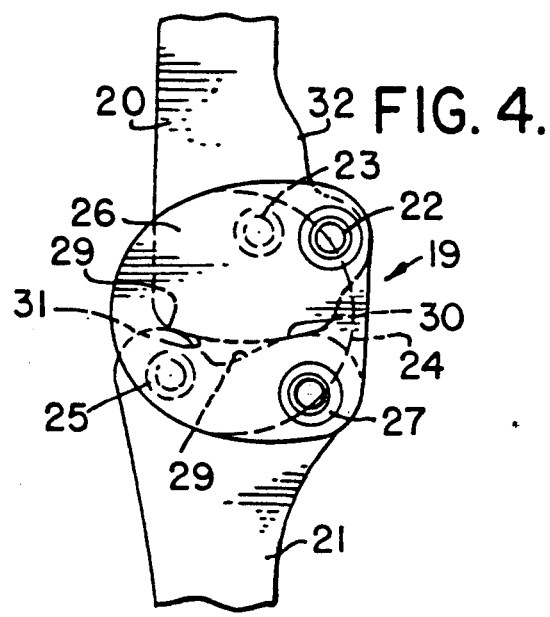
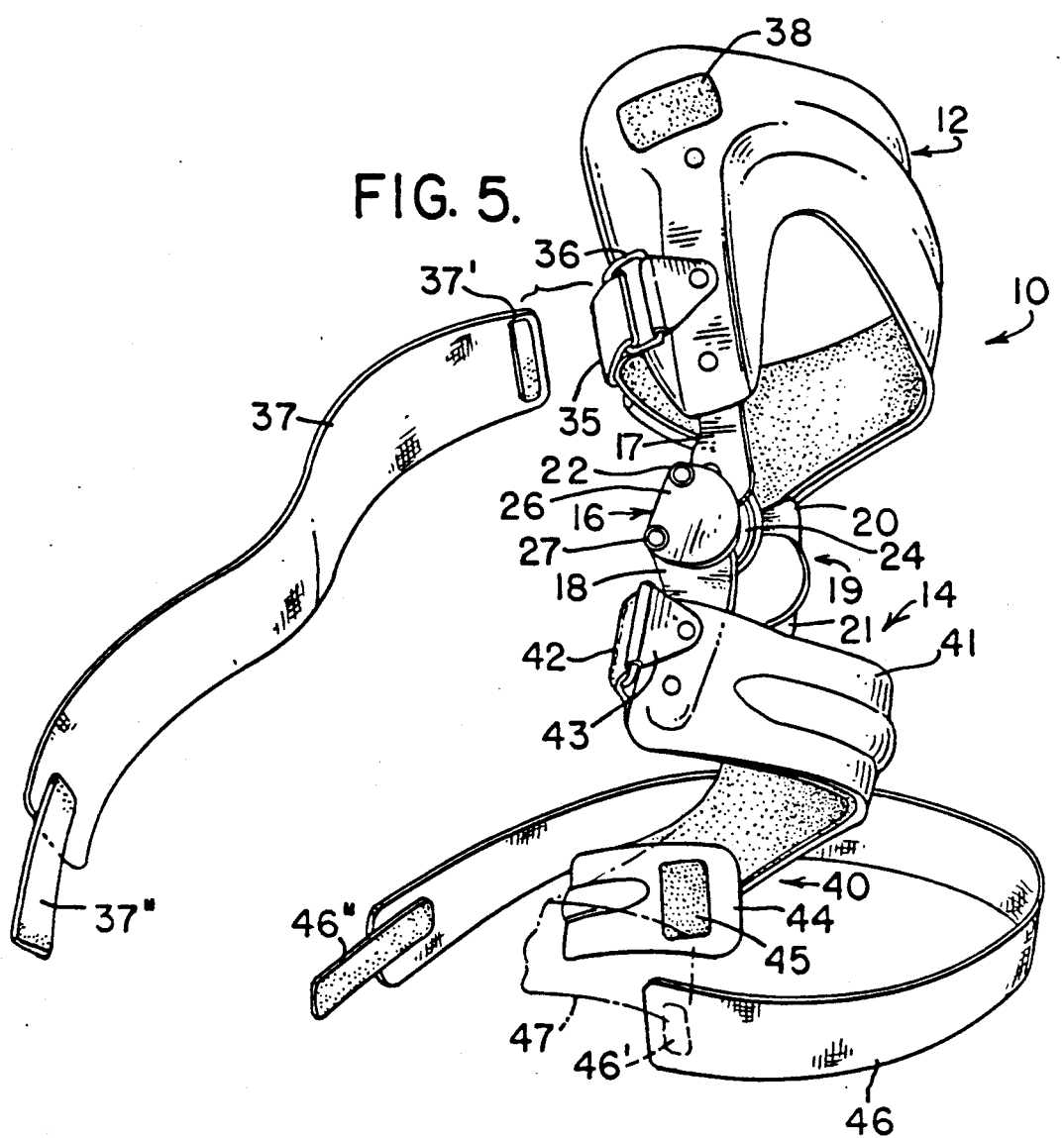

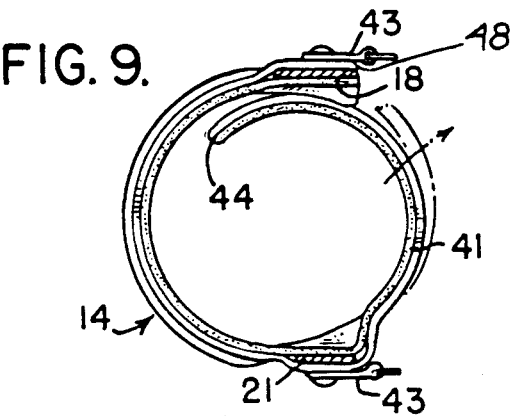
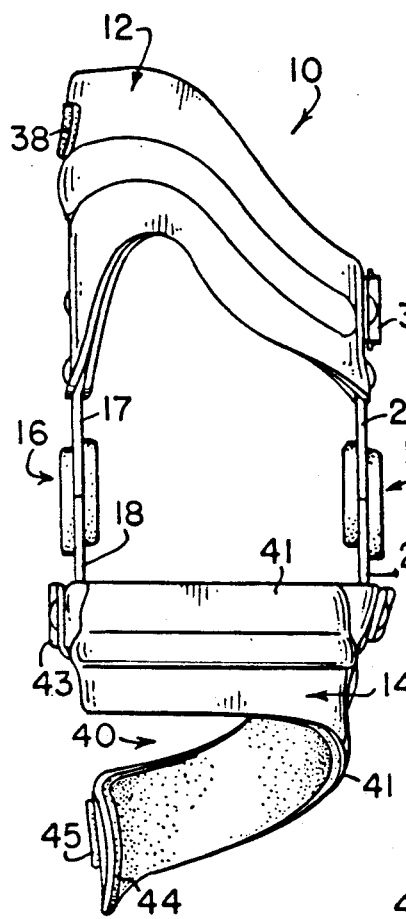
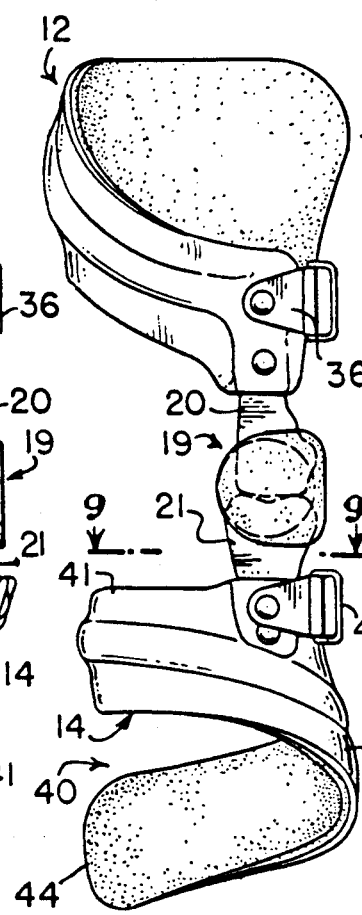
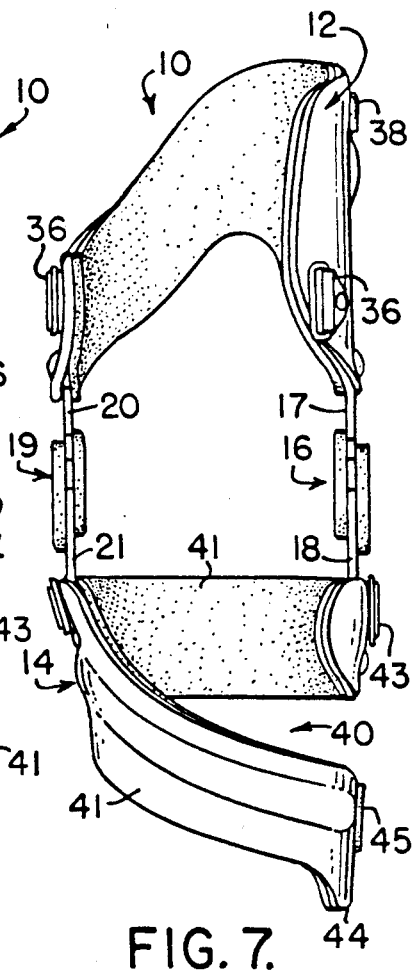
FIG. 9.
FIG. 6.   FIG. 8.   FIG. 7.

5,022,391

KNEE ORTHOSIS

BACKGROUND OF THE DISCLOSURE

The field of the invention is medical appliances, and the invention relates more particularly to orthotics. The invention relates still more particularly to knee braces of the type useful for athletes and post-op, post-injury patients, particularly those with damaged anterior cruciate ligament (ACL) injury.

Many new post-injury knee orthoses have appeared on the market, and many such braces have found widespread use and have enabled the users to prevent further knee injury. The effectiveness of such knee braces differs widely, however, and factors such as comfort, stability, restrictiveness, suspension, weight, appearance, durability, price availability and service are all factors which must be considered. Even the most scientifically designed brace will be of no benefit if the patient dislikes wearing it, or if it is very time consuming to secure.

A pair of related patents have recently issued showing a knee brace of the general type discussed below, namely, U.S. Pat. Nos. 4,723,539 and 4,773,404. Under load and at a 30° s of flexion, however, there is eight millimeters of anterior draw in the hinge alone. It has been found that such hinge permits excessive translocation of the tibia by following the motion of the tibia rather than by guiding it.

SUMMARY OF THE INVENTION

It is an object of the present invention to provide a light-weight, comfortable, durable and stable hinge which tends to initiate a posteriorly directed force on the tibia as it begins to flex, thereby guiding the tibia in a motion which keeps it in its proper position.

The present invention is for an improved knee orthosis of the type having a femoral shell having a medial femoral upright and a lateral femoral upright affixed thereto, a tibial shell having a medial tibial upright and a lateral tibial upright affixed thereto, and means for hinging the medial uprights together and means for hinging the lateral uprights together, together with straps to hold the shells in place. The improvement of the present invention comprises a medial hinge and a lateral hinge, each of said hinges having a pair of femoral pins comprising an anterior femoral pin and a posterior femoral pin. The pair of femoral pins are affixed to the femoral upright near the base thereof. A pair of tibial pins comprising an anterior tibial pin and a posterior tibial pin, said pair of tibial pins being affixed to said tibial upright near the top thereof. A first link plate is affixed to said anterior femoral pin and to said anterior tibial pin, and a second link plate is affixed to said posterior femoral pin and to said posterior tibial pin. The femoral upright and the tibial upright are co-planar. The present invention further includes an improved tibial shell which has a C-shaped portion to which the tibial uprights are attached and which extends over the anterior of the tibia. A spiral portion extends downwardly and spirally from one end of the C-shaped portion subtending at least 180° from the hinge from which it extends. Preferably, the pair of femoral pins are oriented about horizontally when the femoral upright is vertical, and the pair of tibial pins is also oriented about horizontally when the tibial upright is vertical. Also, the rotational movement is preferably limited by contact between the base of the femoral upright and the top of the tibial upright.

BRIEF DESCRIPTION OF THE DRAWINGS

FIG. 1 is a perspective view showing the knee brace of the present invention strapped to the right knee of a patient.

FIG. 2A is a side view of the medial hinge of the knee brace of FIG. 1 showing an initial deflection of the tibial upright in phantom view.

FIG. 2B is a side view of the medial hinge of FIG. 2A showing progressive movement of the femoral upright and the tibial upright.

FIG. 2C is a side view of the medial hinge of FIG. 2A showing progressive movement of the femoral upright and the tibial upright.

FIG. 2D is a side view of the medial hinge of FIG. 2A showing progressive movement of the uprights in their maximum flexure position.

FIG. 3 is a front view of the hinge of FIG. 2.

FIG. 4 is a reverse side view of the hinge between the medial femoral upright and medial tibial upright showing the opposite side as that shown in FIG. 2.

FIG. 5 is a perspective view of the left side of the knee brace of FIG. 1.

FIG. 6 is a front view thereof.

FIG. 7 is a rear view thereof.

FIG. 8 is a left side view thereof.

FIG. 9 is a cross-sectional view taken along line 9—9 of FIG. 8.

DESCRIPTION OF THE PREFERRED EMBODIMENTS

The knee brace of the present invention is shown in FIG. 1 and indicated generally be reference character 10. Brace 10 is strapped about the right leg 11 of the wearer. Brace 10 has a femoral shell 12 strapped about the thigh 13 of the wearer, and a tibial shell 14 strapped about the calf and tibia 15 of the wearer.

Attempts at duplicating the complex kinematics of the knee with external mechanisms have been, if anything, mildly successful. The primary function of any knee orthosis should be the control of anterior tibial excursion. Without stabilization of this motion, loads placed on the anterior cruciate ligament and secondary structures of the knee are greatly increased. The need for a mechanically correct hinge is crucial before attempting to brace the anterior cruciate ligament deficient knee. Upon close examination, geared polycentric and single access hinges encourage anterior tibial excursion as the knee flexes. The hinge of the present invention more closely approximates the kinematics necessary to stabilize the anterior cruciate ligament deficient knee because the hinge of the present invention provides for posterial tibial shift without a tendency toward shear while in flexion. Each knee brace has a lateral hinge 16 which includes a lateral femoral upright 17 and a lateral tibial upright 18. Medial hinge 19 similarly has a medial femoral upright 20 and a medial tibial upright 21. The medial hinge 19 is shown in detail in FIGS. 2, 3 and 4. The lateral hinge 16 would be a mirror image of the medial hinge.

As shown in FIG. 2A medial hinge 19 has a medial femoral upright 20 which includes a pair of femoral pins, namely, a posterior femoral pin 22 and an anterior femoral pin 23. Anterior femoral pin 23 also passes through an inner link 24. Inner link 24 is preferably circular and is also connected to an anterior tibial pin 25. Anterior tibial pin 25 also passes through the medial tibial upright 21 near the top thereof.

Posterior femoral pin 22 passes through an outer disk 26 shown best in FIG. 4. A posterior tibial pin 27 is rotatingly connected to outer link 26 as well as to the upper portion of medial tibial upright 21. The link is shown in front view in FIG. 3 where it can be seen that the medial femoral upright 20 is aligned with the medial tibial upright 21.

The unique motion of the hinges of the present invention is shown best in FIGS. 2A through 2D. In the upright position, shown in FIG. 2A, it can be seen that the bottom 28 of the femoral upright 20 contacts the top 29 of the tibial upright 21 at points 30 and 31. Similarly, as the hinge is flexed, as shown in FIG. 2D, the top 29 of tibial upright 21 contacts the femoral upright at a point indicated at reference character 32. This, of course, stops further flexure.

Most importantly, it can be seen by the phantom view in FIG. 2A that the tibia is urged rearwardly at the initiation of flexure. This prevents a subluxing forward of the tibia which is the most common disfunction of the anterior cruciate ligament deficient knee.

It can be seen in FIG. 2A that when the femoral and tibial uprights are in their position of maximum extension that the anterior femoral pin 23, the posterior tibial pin 27 and the anterior tibial pin 25 form about an equilateral triangle. It can also be seen that the pair of femoral pins 22 and 23 are about horizontal as are the pair of tibial pins 25 and 27. By this positioning, it has been found that the links securely support and guide the movement of the two uprights in a particularly desirable motion. It is also noted that inner link 24 goes through a lesser rotary movement than does outer link 26. Thus, it is preferable, although not essential, that the inner link be placed on the inner surface of the hinge. It should also be noted that both of the femoral pins 22 and 23 are behind the central axis 20' of the femoral upright and that the tibial pins are on opposite sides of the central axis 21' of the tibial upright 21. Preferably, the femoral pins are about 9/16ths of an inch apart and the tibial pins are about 1 and 1/16th inches apart. Furthermore, preferably, the femoral pins are about 1½ th inches above the tibial pins.

The constructions of the femoral and especially the tibial shell 12 and 14 form another important feature of the present invention. These are shown best in FIGS. 5 through 9. A right side view of the hinge of the present invention is shown in FIG. 5. Femoral shell 12 and tibial shell 14 are preferably fabricated from a thermoplastic polymer so that they may be vacuum formed. This provides both a lightweight, strong and aesthetically attractive material. High density polyethylene has been found effective for this purpose. The hinge material is preferably fabricated from high tensile strength aircraft aluminum, and this is preferably covered with a sponge pad both for aesthetics as to the outer link and for comfort as to the inner link. Likewise, the shells are laminated with a sponge material for comfort and also to assist in holding the shells in place.

In FIG. 5, it can be seen that femoral shell 12 is securable to the wearer by a lower strap 35 which is affixed by a conventional buckle 36 riveted to shell 12. Lower strap 35 is advantageously secured with Velcro type of attachment. A wide upper strap 37 is preferably made from an elastic material so that it may give with the flexure of the quadrilateral muscles and the hamstring muscles. Strap 37 is, likewise, preferably secured to shell 12 by Velcro, portions of which are indicated by reference characters 37' and 37". This is preferably obtained by the affixing of a layer of hook material 38 to the side of shell 12 and then providing a wide elastic strap 37 which has pile material 37' at one end for connection to hook material 38 and hook material 37" at the other end for connection to the exterior of strap 37, itself.

Lower shell 14 has a spiral design which is indicated generally by reference character 40. Shell 14 has a C-shaped portion 41 to which an upper strap 42 is held through loop 43. The spiral portion extends downwardly and circularly around the calf region of the wearer and terminates at its lower end 44. A rectangle of hook material 45 is affixed near the terminus 44 of spiral 40. A lower elastic strap 46 has a section of pile material 46' for affixing to hook material 45. The strap is then wound around the calf and, as with strap 37, has a layer of hook material 46" at its outer end which is attachable to the outer surface of strap 46. This spiral construction assists in securing the tibia against anterior tibial excursion. It is also easy to affix over the tibia since it is capable of flexing, as shown by phantom line 47, whereby the ankle can be easily passed through the space between the lower part of the spiral and the C-shaped portion of shell 14. As shown in FIG. 9, it can be seen that the spiral extends more than 360° from its point of beginning indicated by reference character 48.

The knee orthosis of the present invention is especially comfortable and this helps assure patient compliance. It is attractive in appearance because of its smooth, modern lines and the novel hinge construction. It withstands the rigors of today's athlete and is quickly applied and removed.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. An improved knee orthosis of the type having a femoral shell having a medial femoral upright and a lateral femoral upright affixed thereto, a tibial shell having a medial tibial upright and a lateral tibial upright affixed thereto, and means for hinging the medial uprights together, and means for hinging the lateral uprights together, and straps to hold the shells in place, each brace having a medial hinge and a lateral hinge wherein the improvement comprises:

a medial hinge and a lateral hinge, each of said hinges having a pair of femoral pins comprising an anterior femoral pin and a posterior femoral pin, said pair of femoral pins being affixed to the femoral upright near the base thereof, a pair of tibial pins comprising an anterior tibial pin and a posterior tibial pin, said pair of tibial pins being affixed to said tibial upright near the top thereof, a first link plate affixed to said anterior femoral pin and to said anterior tibial pin, and a second link plate affixed to said posterior femoral pin and to the posterior tibial pin and said femoral upright and said tibial upright being co-planar and said anterior and posterior femoral pins being substantially horizontal when said tibial and femoral links are about vertical thereby preventing anterior tibial excursion.

2. The improved knee orthosis of claim 1 wherein the anterior femoral pin, the posterior tibial pin and the anterior tibial pin form about an equilateral triangle when the femoral and tibial links are about aligned.

3. The improved knee orthosis of claim 2 wherein the posterior femoral pin is positioned rearwardly with respect to said posterior femoral pin.

4. The improved knee orthosis of claim 3 wherein the posterior femoral pin is closer to the anterior femoral pin than the posterior tibial pin is to the anterior tibial pin.

5. The improved knee orthosis of claim 4 wherein said femoral pins are about 9/16ths of an inch apart and the tibial pins are about 1 1/16th inches apart.

6. The improved knee orthosis of claim 5 wherein the femoral pins are about 1⅛th inches above the tibial pins when the femoral and tibial uprights are aligned.

7. The improved knee orthosis of claim 1 wherein said first link is about circular.

8. The improved knee orthosis of claim 1 wherein the femoral upright has a femoral central axis, and both femoral pins are positioned rearwardly with respect to said femoral axis.

9. The improved knee orthosis of claim 8 wherein the tibial upright has a tibial central axis, and the anterior tibial pin is positioned in front of the tibial axis and the posterior tibial pin is positioned rearwardly with respect to said tibial axis.

10. An improved knee orthosis of the type having a femoral shell having a medial femoral upright and a lateral femoral upright affixed thereto, a tibial shell having a medial tibial upright and a lateral tibial upright affixed thereto, and means for hinging the medial uprights together and means for hinging the lateral uprights together, and straps to hold the shells in place, each brace having a medial hinge and a lateral hinge wherein the improvement comprises:
a medial hinge and a lateral hinge, each of said hinges having a pair of femoral pins comprising an anterior femoral pin and a posterior femoral pin, said pair of femoral pins being affixed to the femoral upright near the base thereof, said pair of femoral pins being oriented substantially horizontally when the femoral upright is vertical, a pair of tibial pins comprising an anterior tibial pin and a posterior tibial pin, said pair of tibial pins being affixed to said tibial upright near the top thereof, said pair of tibial pins being oriented about horizontally when said tibial upright is vertical, an inner link plate affixed to said anterior femoral pin and to said anterior tibial pin, and an outer link plate affixed to said posterior femoral pin and to the posterior tibial pin and said femoral upright and said tibial upright being co-planar thereby preventing anterior tibial excursion.

11. The improved knee orthosis of claim 10 wherein the rotation of the femoral upright with respect to the tibial upright being limited by the contact between the base of the femoral upright and the top of the tibial upright.

12. The improved knee orthosis of claim 11 wherein the anterior femoral pin, the anterior and posterior tibial pins are oriented to form about an equilateral triangle when the femoral and tibial uprights are about aligned.

13. The improved knee orthosis of claim 12 wherein the anterior and posterior femoral pins are both positioned behind the central axis of the femoral upright.

14. An improved knee orthosis of the type having a femoral shell having a medial femoral upright and a lateral femoral upright affixed thereto, a tibial shell having a medial tibial upright and a lateral tibial upright affixed thereto, and means for hinging the medial uprights together, and means for hinging the lateral uprights together, and straps to hold the shells in place, each brace having a medial hinge and a lateral hinge, said improved knee orthosis being placed on the knee of a wearer having a femur and a tibia wherein the improvement comprises:
the tibial shell has a C-shaped portion to which the tibial uprights are attached, and a spiral portion extends downwardly and spirally from one end of the C-shaped portion subtending at least about 360° from the hinge from which it extends and ends at a terminus adjacent the tibia of the wearer and strap means affixed to said C-shaped portion, said strap means encircling the wearer's tibia and also surrounding the terminus of the C-shaped portion.

15. The improved knee orthosis of claim 14 wherein said tibial shell is fabricated from a non-reinforced flexible polymer.

16. The improved knee orthosis of claim 15 wherein said polymer is high density polyethylene.

17. The improved knee orthosis of claim 14 wherein said tibial shell spirals downwardly from the position adjacent the medial hinge.

18. An improved knee orthosis of the type having a femoral shell having a medial femoral upright and a lateral femoral upright affixed thereto, a tibial shell having a medial tibial upright and a lateral tibial upright affixed thereto, and means for hinging the medial uprights together and means for hinging the lateral uprights together, and straps to hold the shells in place, each brace having a medial hinge and a lateral hinge wherein the improvement comprises:
a medial hinge and a lateral hinge, each of said hinges having a pair of femoral pins comprising an anterior femoral pin and a posterior femoral pin, said pair of femoral pins being affixed to the femoral upright near the base thereof, a pair of tibial pins comprising an anterior tibial pin and a posterior tibial pin, said pair of tibial pins being affixed to said tibial upright near the top thereof, an inner link plate affixed to said anterior femoral pin and to said anterior tibial pin, and an outer link plate affixed to said posterior femoral pin and to the posterior tibial pin and said femoral upright and said tibial upright being co-planar;
wherein the tibial shell has a C-shaped portion to which the tibial uprights are attached, and a spiral portion extends downwardly and spirally from one end of the C-shaped portion subtending at least about 360° from the hinges from which it extends, said C-shaped portion ending in a terminus; and
strap means having first and second ends, the first end of said strap means being affixed to said C-shaped portion adjacent said terminus, and the second end of said strap means including attachment means for securing said second end of said strap means about a wearer's leg.

* * * * *